United States Patent
Monson et al.

[11] Patent Number: 5,602,091
[45] Date of Patent: Feb. 11, 1997

[54] INSTANTANEOUSLY SELF-FOAMING LIQUID CLEANSING COMPOSITION

[75] Inventors: James A. Monson, Ramsey; Dawn T. Anderson, Minneapolis; James L. Kurtz, Plymouth; Joseph I. Kravitz, Champlin, all of Minn.

[73] Assignee: Dowbrands L.P., Indianapolis, Ind.

[21] Appl. No.: 481,975

[22] Filed: Jun. 7, 1995

Related U.S. Application Data

[62] Division of Ser. No. 365,992, Dec. 29, 1994, abandoned, which is a continuation of Ser. No. 208,004, Mar. 8, 1994, abandoned, which is a continuation of Ser. No. 920,724, Jul. 28, 1992, abandoned.

[51] Int. Cl.$^6$ .................................................. C11D 17/00
[52] U.S. Cl. .......................... 510/406; 510/370; 510/159; 510/140
[58] Field of Search ...................... 220/203.01; 215/16, 215/311; 222/402.21, 96, 92, 107; 252/90, 173, 174.15, 174.23, 153, 550, DIG. 13; 424/43, 73; 520/406, 370, 159, 140

[56] References Cited

U.S. PATENT DOCUMENTS

| | | | |
|---|---|---|---|
| 2,357,544 | 9/1944 | Prance | 222/96 |
| 2,655,480 | 10/1953 | Spitzer et al. | 252/90 |
| 2,694,507 | 11/1954 | Elliot | 222/92 |
| 2,927,717 | 3/1960 | McDermott | 222/213 |
| 2,995,521 | 8/1961 | Estingnard-Bluard | 252/90 |
| 3,062,751 | 11/1962 | Wahlin et al. | 252/305 |
| 3,154,224 | 10/1964 | Wakeman | 222/394 |
| 3,541,581 | 11/1970 | Monson | 252/90 |
| 3,728,265 | 4/1973 | Cella et al. | 252/90 |
| 3,981,415 | 9/1976 | Fowler et al. | 222/95 |
| 4,113,643 | 9/1978 | Thompson et al. | 252/90 |
| 4,145,411 | 3/1979 | Mende | 424/45 |
| 4,258,865 | 3/1981 | Vahl et al. | 222/213 |
| 4,322,018 | 3/1982 | Rutter | 222/83 |
| 4,428,512 | 1/1984 | Nosek | 222/402.15 |
| 4,450,985 | 5/1984 | Beard | 222/402.22 |
| 4,528,111 | 7/1985 | Su | 252/107 |
| 4,587,030 | 5/1986 | Casey | 252/92 |
| 4,597,425 | 7/1986 | Tally | 150/55 |
| 4,726,944 | 2/1988 | Osipow et al. | 424/70 |
| 4,744,979 | 5/1988 | Osipow et al. | 427/73 |
| 4,772,427 | 9/1988 | Dawson et al. | 252/559 |
| 4,871,530 | 10/1989 | Grollier et al. | 424/47 |
| 4,931,204 | 6/1990 | Ramirez et al. | 252/167 |
| 5,002,680 | 3/1991 | Schmidt et al. | 252/90 |
| 5,063,051 | 11/1991 | Grollier et al. | 424/70 |
| 5,091,111 | 2/1992 | Neumiller | 252/305 |

(List continued on next page.)

FOREIGN PATENT DOCUMENTS

| | | |
|---|---|---|
| 1007282 | 5/1952 | France . |
| 2332497 | 1/1974 | Germany . |
| 8603567 | 7/1986 | Spain . |
| 975605 | 11/1964 | United Kingdom . |
| 8603405 | 6/1986 | WIPO . |
| 9005774 | 3/1990 | WIPO . |

OTHER PUBLICATIONS

Soap Perfumery and Cosmetics, vol. 53, No. 1, Jan. 1980, London pp. 19–25, J. Blakeway "A Comparative Study of Alternative Propellants to the Chlorofluorocarbons in Aerosols".

*Primary Examiner*—Douglas J. McGinty
*Assistant Examiner*—Michael P. Tierney

[57] ABSTRACT

The present invention relates to a self-foaming, self-leveling aqueous liquid composition packagable in a non-pressurized deformable dispenser of flexible barrier material adapted to contain, maintain and dispense a proportioned amount of the cleansing composition under positive pressure. The composition comprises: a major amount of water; a surfactant; and a dual purpose pressure agent comprising at least one aliphatic hydrocarbon fluid in amounts sufficient to provide the liquid composition, which when contained in a dispenser exerts a positive vapor pressure at least at about 1.6° C. The composition is dispensed as a liquid under normal operating conditions, which liquid foams instantaneously and spontaneously on spreading.

4 Claims, 2 Drawing Sheets

U.S. PATENT DOCUMENTS

| | | | |
|---|---|---|---|
| 5,160,665 | 11/1992 | Owada et al. | 252/307 |
| 5,186,857 | 2/1993 | Ramirez et al. | 252/167 |
| 5,232,632 | 8/1993 | Woo et al. | 252/546 |
| 5,234,619 | 8/1993 | Greene et al. | 252/108 |
| 5,248,495 | 9/1993 | Patterson et al. | 424/73 |
| 5,279,819 | 1/1994 | Hayes | 424/73 |
| 5,308,643 | 5/1994 | Osipow et al. | 424/73 |
| 5,322,683 | 6/1994 | Mackles et al. | 424/45 |
| 5,326,556 | 7/1994 | Barnet et al. | 424/73 |
| 5,334,325 | 8/1994 | Chaussee | 252/174.16 |
| 5,346,639 | 9/1994 | Hatfield | 252/90 |
| 5,429,815 | 7/1995 | Faryniarz et al. | 424/47 |
| 5,443,817 | 8/1995 | Zimmerman et al. | 424/47 |

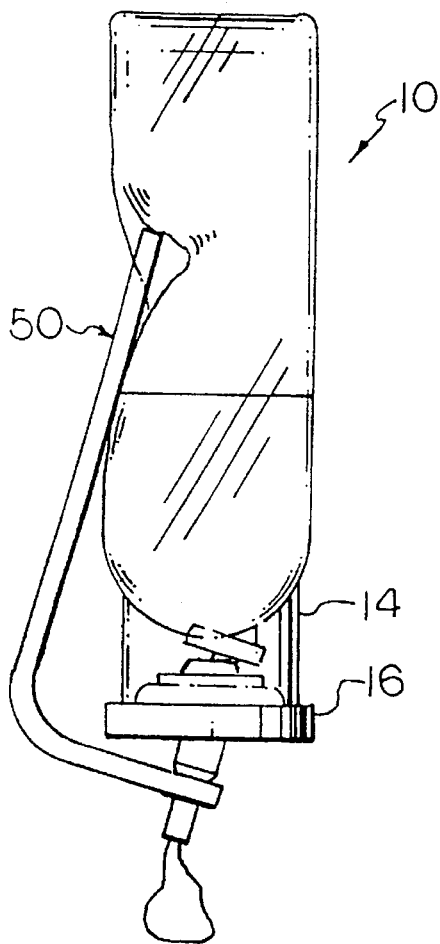
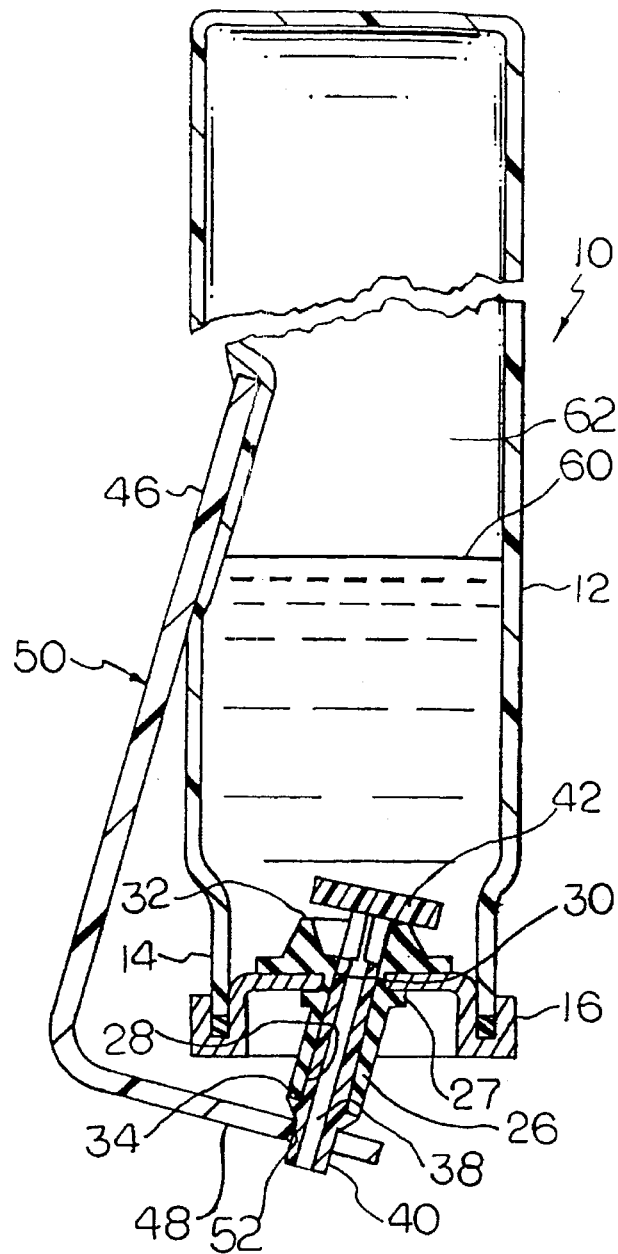
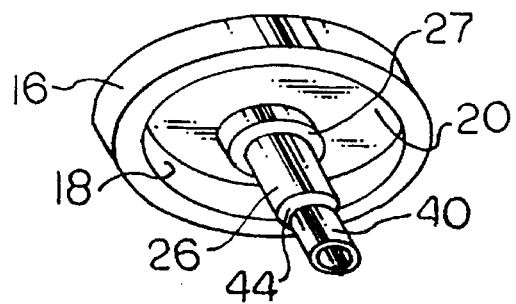

INSTANTANEOUSLY SELF-FOAMING LIQUID CLEANSING COMPOSITION

CROSS-REFERENCE TO RELATED APPLICATION

This is a divisional of application Ser. No. 08/365,992 filed Dec. 29, 1994, which is a continuation of application Ser. No. 08/208,004 filed Mar. 8, 1994, now abandoned which is a continuation of application Ser. No. 07/920,724 filed Jul. 28, 1992 now abandoned.

FIELD OF THE INVENTION

The present invention relates to a novel self foaming aqueous liquid cleansing composition. More particularly, the present invention relates to a liquid cleansing composition which is packagable in a non-pressurized dispenser made of barrier material, which is squeezable and equipped with a positive shut-off valve.

BACKGROUND OF THE INVENTION

Conventional personal care and household cleaning products are available either as solids or as liquids. Solid cleaning products include bar soap, which can be whipped up into a lather by agitation with hands, or a brush in the case of a shaving soap; or powders which are normally first dissolved in water and then agitated to prepare a lather. Bar soaps and powders may cause unsightly residues on sinks, bath tubs and showers if exposed to water. This also results in waste of products.

Liquid cleaning products are generally available as thick liquids, such as shampoos, shower gels, or liquid soaps, which are difficult to foam and take time, dexterity, and special manipulation to dispense from their containers and to foam and lather.

The use of aqueous post foaming compositions in the form of a gel in personal care products such as shaving creams, toothpaste, and shower gels has been known in the art for several years. However, these products are generally packaged in rigid pressurized aerosol containers such as the Sepro™ can or Piston™ cans with propellant gases contained therein. Such aerosol containers are expensive to manufacture and ship. The propellants used therein do not form an integral part of the composition and are typically compartmentalized from the product to provide the positive pressure needed to aid in the dispensation of the product. Such containers are known in the industry as barrier packages because they provide the barrier between the extraneous propellants and the composition to be dispensed. The propellant gases released to the atmosphere by use of such containers are increasingly unacceptable environmentally. The aerosol containers for dispensing post foaming gels typically contain these products under pressures ranging from about 308 kPa to about 420 kPa (about 44 psig to about 60 psig) above the atmospheric pressure at ambient temperatures, and dispense about less than four gram/sec of the product at a given time.

Some personal care products like shaving lathers, and mousses are characteristically dispensed as foams and are contained in the pressurized dispensers designed to maintain or increase the inside vapor pressures of the product from about 350 kPa to about 700 kPa (about 50 psig to about 100 psig) and to dispense between about 5 to about 6 grams/sec of the product at a given time.

U.S. Pat. Nos. 4,726,944, and 4,744,979 disclose post foaming liquid compositions which have vapor pressures less than atmospheric pressure at ambient temperatures. These compositions can be poured onto the skin or other surface, rubbed up to 60 seconds to generate foam.

None of the prior art, however, discloses a self foaming aqueous liquid composition that 1) is packagable in a non-pressurized container of barrier material, 2) contains a pressure agent which forms an integral part of the composition, 3) exerts a positive pressure above atmospheric pressure at ambient temperatures when packaged, and 4) is dispensed as a liquid which foams instantaneously on spreading with a single motion and develops into copious foam.

Moreover, none of the prior art discloses a non-pressurized dispenser of a barrier material with a head space, which is not separated from the product by a barrier. The package is capable of 1) containing a self foaming aqueous liquid composition under positive pressure, i.e., vapor pressure of the composition being above atmospheric pressure but below 280 kPa (40 psig) at ambient temperatures, and 2) dispensing varying amounts of the composition in a liquid form by the operation of a positive shut-off valve.

SUMMARY OF THE INVENTION

It has been discovered that an aqueous liquid composition of the present invention exerts a positive pressure above atmospheric pressure at least at about 1.6° C. and is packagable in a non-pressurized dispenser of barrier material. The liquid composition of the invention is substantially free from foaming before dispensation and is dispensed as a liquid and foams spontaneously and instantaneously when spread on a surface with a single motion, and develops into a rich lather.

In one embodiment, the invention relates to an aqueous self foaming, self-leveling liquid composition, comprising: a major amount of water; a surfactant; and a dual purpose pressure agent comprising at least one aliphatic hydrocarbon fluid in amounts sufficient to provide the composition which when contained in a dispenser exerts a positive vapor pressure at least at about 1.6° C. (about 35° F. the composition being dispensed as a liquid under normal operating conditions, the liquid foaming instantaneously on spreading.

In another embodiment, the present invention relates to a non-pressurized dispenser of a flexible barrier material for the self foaming aqueous liquid composition of the present invention, comprising a vessel formed with deformable peripheral walls, having an open neck, and a closure member associated with the neck of the dispenser, the closure member having a positive shut-off valve member adapted to controllably dispense a proportioned amount of the self-foaming composition in a liquid form.

In still another embodiment, the present invention relates to a package, comprising: (A) a non-pressurized dispenser of a flexible barrier material for an aqueous self foaming liquid composition, the dispenser comprising a vessel formed with deformable peripheral walls, having an open neck, and a closure member associated with the neck of the dispenser, the closure member comprising a positive shut-off valve member adapted to controllably dispense a proportioned amount of the self-foaming, self-leveling composition in a liquid form, the composition being so packaged in the dispenser as to provide a head space above the liquid; and (B) an aqueous self-foaming, self-leveling liquid composition, comprising: a major amount of water; a surfactant; and a dual purpose pressure agent comprising at least one aliphatic hydrocarbon fluid in amounts sufficient to provide the composition which exerts a positive vapor pressure against the peripheral walls of the dispenser at least at about 1.6° C.; the composition being dispensed as a liquid under normal operating conditions, the liquid foaming instantaneously on spreading.

BRIEF DESCRIPTION OF THE DRAWINGS

In describing the invention in detail, reference will be made to the accompanying drawings in which:

FIGS. 2A and 2B are perspective opposing ends on views of the closure member for the dispenser of FIG. 1.

FIG. 4 is a similar to FIG. 1 taken while the dispenser is in operation.

FIG. 5 is a longitudinal cross section of the dispenser of FIG. 4 taken along line 5—5 of FIG. 4.

SELF FOAMING SELF-LEVELING LIQUID COMPOSITION

Figure 1:
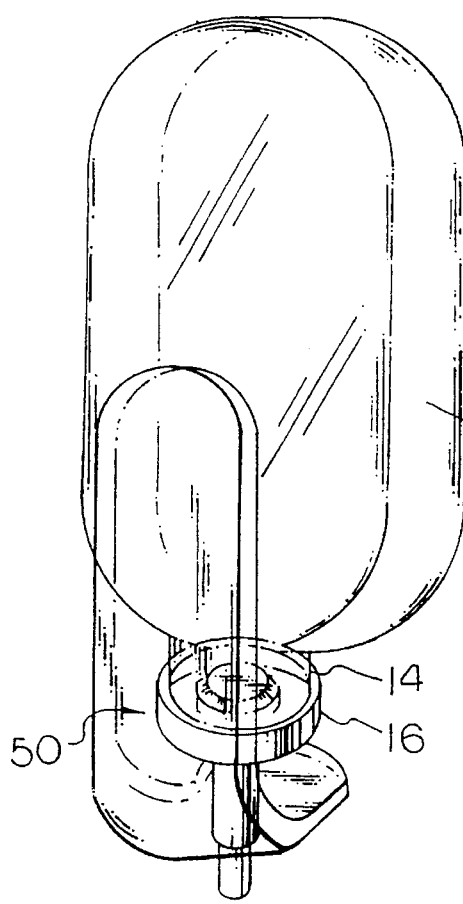
FIG. 1 is a schematic front elevational view of a preferred embodiment of a dispenser of fast-foaming liquid composition in accordance with this invention.

"Self-leveling liquid composition" for purposes of the present invention is defined as the composition which remains free from foaming inside the dispenser under varying ambient temperatures and pressures, and includes flowable Newtonian liquids, thixotropic liquids, and thin gels, which flow to the bottom of the dispenser as the dispenser is inverted.

"Self foaming" liquid composition, as described herein, refers to the composition which is dispensed as a liquid under normal operating conditions, and not as a foam. The liquid foams spontaneously, and instantaneously on spreading with a single motion.

Normal operating conditions involve a broad range of temperature variations that are encountered by the consumer for the intended use of the composition as well as those encountered in shipping, warehousing and merchandising, Water is a major essential component of the composition of the present invention. Water is necessary to provide both the desired foaming and the lathering qualities and is used in quantities sufficient to obtain the liquid of desired viscosity. It has been found that at least about 50 percent and preferably from about 60 to about 80 percent by weight of the composition should be water, although higher amounts may be employed if desired,. e.g., up to about 95 percent by weight of the total composition.

An essential component of the post foaming composition of the present invention is at least one surface active agent present in an amount from about 0.1% to about 60% by weight of the composition. It has been found that any nonionic, anionic, or amphoteric surfactants, when used alone, will provide the composition of the invention. When more than one surfactant is used, a mixture of the surfactants selected from anionic, nonionic, cationic, and amphoteric surfactants will provide the composition of the invention. Numerous surface active agents or surfactants, suitable for use in the present composition, are described in detail in McCutcheon's "Emulsifiers and Detergents", 1991. Preferably, the surface active agent is present in an amount from about 1.0 to about 30.0% by weight, based on the weight of the composition.

Another essential ingredient of the composition is a dual purpose pressure agent which forms an integral part of the composition. The dual purpose pressure agent is equilibrated between the liquid phase and the gas phase in the head space above the liquid phase in the dispenser. In the liquid phase, the dual purpose agent is present in suspended, emulsified, dispersed, or solubilized form. The dual purpose pressure agent fulfills two purposes: first purpose being that it function as a dispensing aid, and the second purpose being that it function as a foaming aid.

The dual purpose pressure agent functions as a dispensing aid by providing a composition which exerts a positive vapor pressure from about 0.7 kPa to about 280 kPa (0.1 to about 40 pounds per square inch) above the atmospheric pressure at least at about 1.6° C. and above. The equilibrium vapor pressure of the dual purpose pressure agent in the head space of the dispenser effects the dispensation of the composition from the dispenser. The positive pressure in the head space is maintained by a shift in the equilibrium vapor pressure of the pressure agent each time the valve is actuated.

The use of the dual purpose agent as described hereinabove eliminates the need for the expensive compartmentalized aerosol containers of the prior art, and the use thereby of excess propellant gases needed to maintain the higher positive pressures for dispensation of the product contained therein.

The dual purpose pressure agent functions as a foaming aid in that it volatilizes spontaneously on dispensation causing the composition to foam instantaneously on spreading with a single motion and to develop into a rich lather.

The dual purpose pressure agent comprises at least one aliphatic hydrocarbon fluid which is a liquefiable gas or a gaseous hydrocarbon at room temperature. The gaseous hydrocarbon is preferably selected from isobutane, butane, and neopentane. The dual purpose pressure agent may further comprise at least one non-polar liquid which is substantially insoluble in water. Numerous water-insoluble non-polar liquids are described in detail in McCutcheon's "Functional Ingredients", 1991.

"Substantially insoluble" as used herein means liquids which are less than about 0.1% by weight soluble in water.

The water-insoluble non-polar liquid may be a substantially water insoluble nonvolatile silicone oil. The silicone oil includes polyalkylsiloxanes, polyarylsiloxanes, polyalkyarylsiloxanes, polysiloxane gums, dihydroxypolysiloxane, and polyethersiloxane copolymers.

The water-insoluble non-polar liquid is preferably an aliphatic hydrocarbon which exists as a liquid at room temperature, or is a liquid hydrocarbon. Illustrative but not limiting of the liquid hydrocarbons include: isopentane, pentane, n-hexane, isohexane, 2,3-dimethylbutane, and mineral oil.

The vapor pressure of the aliphatic hydrocarbon fluids is primarily responsible for the vapor pressure of the composition. It has been found that higher the vapor pressure of the composition, the more rapidly the lather develops, but the composition may also be dispensed as a foam. It is essential for the purposes of this invention that the composition be substantially free from foaming, and is a liquid before and at the time of dispensation. The hydrocarbons may be so selected as to provide a composition exerting a positive pressure at least at about 1.6° C. It is preferred that the compositions exert a positive pressure at least at about 13°

C. (55° F.). Most preferred compositions are those that exert a positive pressure at least at about 22° C. The choice of suitable hydrocarbons, alone or in combination; the concentration of hydrocarbons in the composition; and the relative ratios of component hydrocarbons if more than one hydrocarbon is used, are therefore, very critical to obtain the composition of the invention.

The weight ratio of the gaseous hydrocarbon to water-insoluble liquid generally varies in range from about 5:95 to about 50:50. Preferably the weight ratio of the gaseous hydrocarbon to water-insoluble liquid varies in range from about 10:90 to about 20:80. The dual purpose pressure agent typically comprises from about 1% to about 20% by weight of the composition.

Preferably, the dual purpose pressure agent is a single gaseous hydrocarbon, which is neopentane. It is suitably present in an amount from about 1% to about 5% by weight, based on the weight of the composition.

More preferably, the dual purpose pressure agent is a mixture of iso-butane or n-butane and a nonvolatile silicone oil. The nonvolatile silicone oil is preferably dimethicone.

Most preferably, the dual purpose pressure agent is a mixture of at least one gaseous hydrocarbon selected from n-butane and iso-butane and at least one liquid hydrocarbon selected from iso-pentane, n-pentane, 2-3,dimethylbutane, n-hexane, isohexane, and mineral oil. The weight ratio of the gaseous hydrocarbon to liquid hydrocarbon typically varies in range from about 0.5:99.5 to about 99.5:0.5. Preferably the weight ratio of the gaseous hydrocarbon to liquid hydrocarbon is in the range from about 10:90 to about 20:80. The most preferred ratio is 20:80.

The composition of the present invention may also contain minor amounts of conventional additional ingredients to impart desired characteristics to the composition. Suitable additives include thickening agents, coloring agents, perfumes, preservatives, antiseptic agents, antibacterial agents, disinfectants, emollients, humectants, and the like. The composition may optionally contain a suspending agent or a thickening agents for imparting desired viscosity to the composition. Suitable thickening agents include carboxy vinyl polymers available as a variety of Carbopols or Carbomers from B. F. Goodrich Company, sodium polacrylate, hydroxyethyl cellulose, guar gum, Xanthum gum and the like. The composition may desirably contain conditioning agents such as Permethyl 104A, a highly branched hydrocarbon available from Presperse; glycerinel guar hydroxypropyl trimonium chloride; fatty acid esters; and the like.

The compositions of the present invention are useful for a variety of topical applications including personal cleaning, household cleaning, as well as shaving preparations. These compositions are particularly useful in shower to be used in lieu of bar soaps and shampoos.

The following examples are illustrative of the composition of the present invention and is not intended as limitation of this invention, many apparent variations of which are possible without departing from the spirit and scope thereof. The stated amounts of the ingredients are parts by weight unless otherwise indicated.

EXAMPLES 1–4

The Examples 1–4 shown in Table I, illustrate the use of a single surface active agent, water and a pressure agent as a single component or as a mixture of components or a blend.

Surfactant Solution

In these Examples 1–4, a surfactant solution was prepared by mixing the stated quantities of the surfactants and water.

Dual Purpose Pressure Agent

The stated amounts of the pressure agent, as a single hydrocarbon or a mixture of hydrocarbons or a blend is cooled to below 5° C., and mixed the above prepared surfactant solution via vigorous manual or mechanical shaking. The mixture is filled into an appropriate dispenser and immediately sealed. Care is taken to avoid entrapping air during this operation.

Pressure Measurement

The vapor pressure exerted by the composition in the dispenser was measured as below:

An Instron was set to measure the load (force) required to deform a flexible walled dispenser filled with the composition. The dispenser was placed lengthwise on a table, and the Instron pushed down from the top so as to push against the head space of the dispenser. The load measurements were then calibrated using the similar dispensers which were pressurized with a known head space pressure (psig) of nitrogen.

The pressure exerted by the composition in the dispenser may also be measured by attaching a pressure guage to the valve of the dispenser. Care should be taken to minimize the introduction of oxygen from the air into the head space of the dispenser.

TABLE I

| Examples | Parts by weight | | | |
| --- | --- | --- | --- | --- |
|  | 1 | 2 | 3 | 4 |
| Surfactant Solution | | | | |
| Water | 97 | 97 | 60 | 60 |
| Potassium Cetyl Sulfate (100% active) | 3 | 3 | — | — |
| Oleamine Oxide (50% active) | — | — | 40 | 40 |
| Pressure Agent | | | | |
| Neopentane | 3 | — | — | — |
| Isobutane | — | 1.8 | 0.6 | — |
| Isopentane | — | — | 2.4 | — |
| Mineral Oil (100% active) | — | 1.2 | — | 2.1 |
| n-Butane | — | — | — | 0.9 |
| Pressure at 22° C. (kPa) (72° F.) | 21 (3 psig) | 14 (2 psig) | 52.5 (7.5 psig) | 28 (4 psig) |
| Pressure at 43° C. (kPa) (110° F.) | 189 (27 psig) | — | — | — |

EXAMPLES 5–8

Examples 5–8 shown in Table II, illustrate use of a blend of two surface active agents, water and a pressure agent blend. The Examples 5–8 are prepared in the manner described above for Examples 1–4.

TABLE II

| Examples | Parts by weight | | | |
|---|---|---|---|---|
| | 5 | 6 | 7 | 8 |
| Surfactant Solution | | | | |
| Water | 54.28 | 44.29 | 56.67 | 70 |
| Ammonium Lauryl Sulfate (anionic) (28% active) | 35.72 | 35.71 | — | — |
| Ammonium[b] Cocoyl Isethionate (anionic) 30% active) | — | — | 33.33 | — |
| Cocamide diethanolamide (nonionic) (100% active) | 10 | — | — | — |
| Cetyl Alcohol (nonionic) (100% active) | — | — | — | 10 |
| Lauroamphodiacetate (amphoteric) (70% active) | — | 20 | — | 20 |
| Isostearyl ethyl-imidoniumethosulfate (cationic) (100% active) | — | — | 10 | — |
| Pressure Agent blend | | | | |
| Isopentane | 2.4 | 2.4 | 2.4 | 2.4 |
| Isobutane | 0.6 | 0.6 | 0.6 | 0.6 |
| Pressure at 22° C. (kPa) (72° F.) | 49 (7 psig) | 56 (8 psig) | 54 (7.7 psig) | 55 (7.9 psig) |

[b]available from PPG Mazer under the name Jordpon ACI.

EXAMPLES 9–12

Examples 9–12 shown in Table III, illustrate the use of a surface active agent, water, a thickening agent, and a pressure agent blend. These examples are prepared by making the surfactant solution by mixing the stated amounts water, surfactant, Carbomer, hydroxyethyl cellulose, and triethanolamine. The pressure agent blend is then added in the manner as described above for Examples 1–4.

TABLE III

| Examples | Parts by weight | | | |
|---|---|---|---|---|
| | 9 | 10 | 11 | 12 |
| Surfactant Solution | | | | |
| Water | 81.39 | 81.39 | 79 | 79 |
| Ammonium Lauryl Sulfate (28% active) | 17.86 | 17.86 | 20 | 20 |
| Carbomer 1342 (100%) active | 0.75 | 0.75 | — | — |
| Hydroxyethyl cellulose (100% active) | — | — | 1 | 1 |
| TEA triethanolamine (99% active) | 0.5 | 0.5 | — | — |
| Pressure agent blend | | | | |
| Isopentane | 1.5 | 4 | 2.4 | 0.9 |
| Isobutane | 1.5 | 1 | 0.6 | 0.1 |
| Pressure at 22° C. (kPa) (72° F.) | 91 (13 psig) | 70 (10 psig) | 87.5 (12.5 psig) | — |
| Pressure at 43° C. (kPg) (110° F.) | — | 182 (26 psig) | — | 112 (16 psig) |

EXAMPLES 13–16

Examples 13–16 shown in Table IV, illustrate the compositions containing a single surfactant, water, a thickening agent, an emollient, and a pressure agent as a single component or a blend of components.

Examples 13–16 are prepared as described below.

Surfactant Solution

Water, surfactant, and Carbomer in stated amounts are mixed together to form a solution, and the solution is heated to a temperature of about 60° C. Permethyl, available from Presperse, in an amount of about 2.0 percent by weight of the composition is added to the heated mixture, and the mixture cooled to room temperature. About 0.5% by weight of the composition of triethanolamine (TEA) is added to the mixture and the mixture is further cooled to below 5° C.

Self Foaming and Pressurizing Agent

The stated amounts of the pressure agent as a single component or a blend of components is cooled to 5° C., and mixed with the surfactant solution prepared above by manual or mechanical shaking. The mixture is filled into an appropriate dispenser and immediately sealed. Care is taken to avoid entrapping air during this operation.

TABLE IV

| Examples | Parts by weight | | | |
|---|---|---|---|---|
| | 13 | 14 | 15 | 16 |
| Surfactant Solution | | | | |
| Water | 77.69 | 77.69 | 77.69 | 77.69 |
| Ammonium Lauryl Sulfate (28% active) | 17.56 | 17.56 | 17.56 | 17.56 |
| Carbomer 1342 (100% active) | 0.75 | 0.75 | 0.75 | 0.75 |
| Isooctahexa-containe PERMETHYL (100% active) | 2 | 2 | 2 | 2 |
| Triethanolamine TEA (100% active) | 0.5 | 0.5 | 0.5 | 0.5 |
| Pressure Agent/Blend | | | | |
| Neopentane | 3 | — | — | — |
| Isopentane | — | 2.6 | — | — |
| Isobutane | — | 0.6 | — | 0.9 |
| n-Butane | — | — | 1.5 | — |
| Mineral oil | — | — | 1.5 | — |
| Dimethicone (100% active) | — | — | — | 2.1 |
| Pressure at 22° C. (kPa) (72° F.) | 52.5 (7.5 psig) | 42 (6 psig) | 119 (17 psig) | 35 (5 psig) |
| Pressure at 43° C. (kPg) (110° F.) | 196 (28 psig) | — | 238 (34 psig) | — |

Examples 1–16 illustrate the composition as comprising water, one or more surfactants, and a pressure agent which is either a single gaseous hydrocarbon, neopentane, or a blend of at least one gaseous hydrocarbon, and at least one water-insoluble non-polar liquid. The compositions so obtained exert a positive pressure at about 22° C. (72° F.).

Package

The stable fast self-foaming liquid composition of the invention is packaged in a non-pressurized dispenser of a barrier material to prevent loss of hydrocarbon vapor to the atmosphere. Suitably, the barrier to loss of vapor must be such that, on the average, the loss of the vapor to the air at about 21° C. (70° F.) in about a year is less than 10% of the original vapor pressure at that temperature.

The barrier material may be a barrier plastic material, metal, glass, or a metal-coated plastic materials like brick packaging used to package carbonated drinks and juices, or laminated tubes with an appropriate barrier layer, and the like. Most preferably, the thermoplastic material used is polyethyleneterepthalate (PET).

The "non-pressurized" dispenser as used herein refers to a dispenser which can be mechanically pressurized but does not contain any propellant other than the aliphatic hydrocarbons which are the integral part of the composition of the invention. The dispenser has a head space above the liquid composition to provide for the vapor of the dual purpose pressure agent. The head space generally comprises from about 2% to about 20% of the volume of the dispenser.

The dispenser may be an aerosol dispenser which is made of metal, non-pressurized, and equipped with a positive shut-off valve.

Preferably, the dispenser is flexible, made of barrier material, comprising a vessel with deformable peripheral walls having an open neck and a closure member comprising a valve member, which is adapted to dispense a proportioned amount of the composition. The deformable nature of the dispenser is preferred since it allows, without the use of gaseous propellants generally used in the art, for the dispensation of essentially the entire contents from the dispenser under varying conditions of temperature and pressure when the flexible side walls or peripheral walls of the dispenser are squeezed.

"A deformable dispenser", as used herein, refers to a noncollapsible resilient dispenser which can be distorted, or squeezed by application of a pressure of about 6.9 to about 20.7 kPa (1–3 psig) and which because of its resiliency or elastic memory or internal pressure from the head space regains its original form, after the external pressure is released.

Preferably, the closure member comprises a positive shut-off valve, which allows for dispensation of varying amounts of the composition with varying vapor pressure under the varying ambient temperature and pressure conditions. The amount of the composition dispensed will generally vary in range from about 4 grams to about 8 grams per second.

A "positive shut-off valve" as employed herein defines a valve which is normally in the sealed position unless the valve is actuated.

The positive shut-off valve, as described hereinbelow in more detail, comprises a tubular valve stem having a central passage for dispensation of the composition and held by a tubular elastic sealing portion mounted in a circular aperture in the wall of the closure member. The sealing portion includes a sleeve portion which extends through the wall of the closure member. The outer sleeve surface seals within the circular aperture, and its inner surface seals about the outer wall of the tubular valve stem. At a level remote from the central aperture, the tubular valve stem and the tubular elastic sealing portions have faces which press against each other and sealingly engage with each other, as illustrated in the drawings hereinafter described.

DETAILED DESCRIPTION OF THE DRAWINGS

Dispenser 10 containing the composition 60 of the invention, including the closure member 16 and its operation is illustrated in FIGS. 1 through 5.

Closed dispenser 10 of FIG. 1 illustrates a preferred embodiment of the invention. Dispenser 10 comprises a continuous open topped vessel 11 having a peripheral wall 12, a neck 14 at one vessel end and a closure member 16 cooperatively engaged with the neck 14.

Figure 2A:
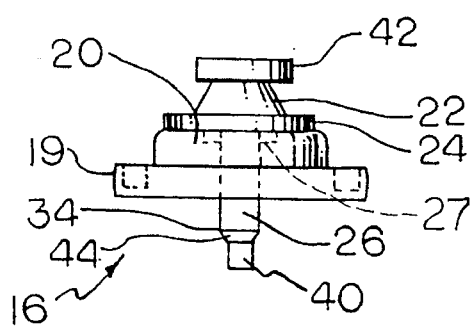

An embodiment of the closure member 16 contemplated to be used with the dispenser 10 of the invention is illustrated in FIGS. 2A, 2B, 3, and 5. The closure member 16 as shown in FIGS. 2A and 2B has a mounting cup 18 having an outstanding rim 19 which sealingly fits over the neck 14 of the dispenser 10. The mounting cup 18 further has a wall portion 20 which serves as the top wall of the dispenser 10. The wall portion 20 includes a circular aperture 21 formed and outwardly flanged about an axis perpendicular to the wall portion 20.

A tubular elastic seal portion 22 includes a seal body portion 24, which is enlarged to provide a large washer-like sealing surface against the inner side of the wall 20 adjacent the aperture 21. The tubular seal portion 22 further includes a sleeve portion 26 extending through the aperture 21 and having an outer sleeve surface 27 bearing sealingly within and against the flange of the circular aperture 21. The tubular seal portion 22 has an inner bore 28, and a lower counter bore 29 which are concentric with the axis a when the sleeve portion 26 is not distorted. The inner bore 28 includes a stem-sealing surface 30 at the level of the circular aperture 21. "Lower" as used herein describes the position of the counterbore relative to the neck 14 of the dispenser when the dispenser is held in upright position.

The seal portion 22 has a valve seating face 32 disposed inwardly of the dispenser 10, and an opposed annular face 34 at the outer end of the sleeve portion 26. The annular face 34 is disposed outwardly of the dispenser.

Figure 3:
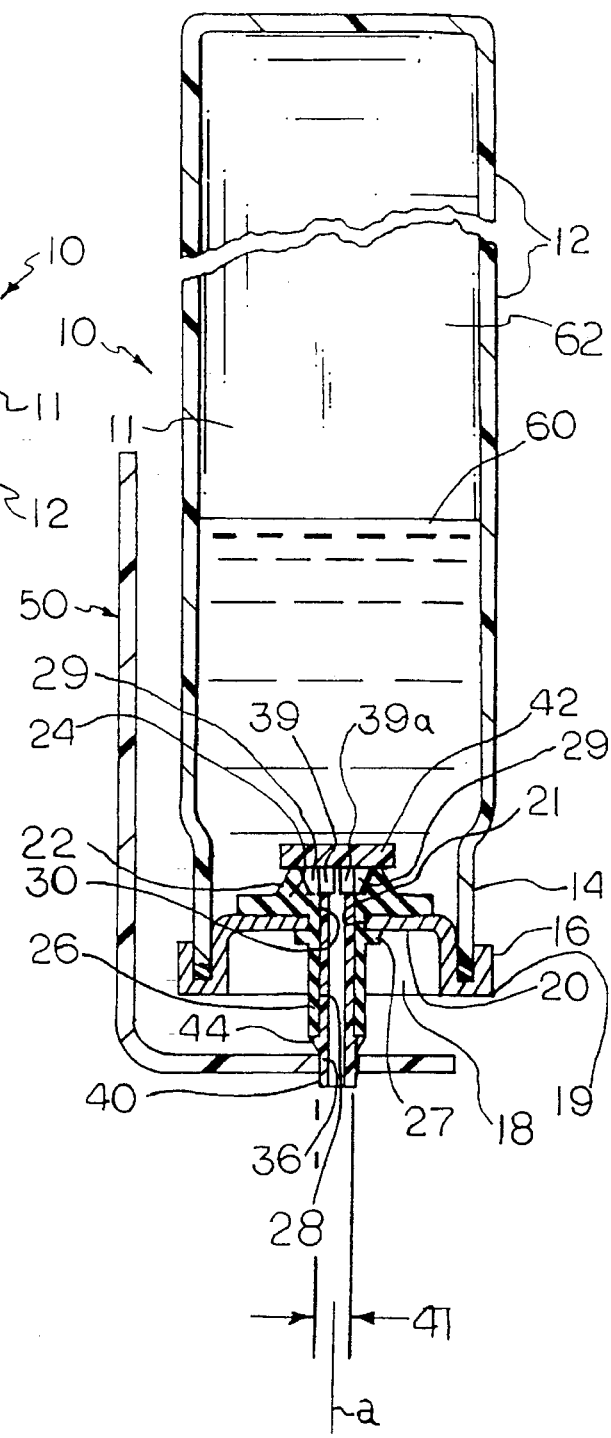
FIG. 3 is a longitudinal cross section of the dispenser of FIG. 1 taken along line 3—3 of FIG. 1.

A tubular valve stem 36 formed of rigid or substantially rigid thermoplastic material as contrasted with the rubbery elastic material of the sealing portion 22 has a central passage 38 for the passage of the contents of the dispenser, and an outer manipulative stem end 40. The valve stem 36 penetrates the sleeve portion 26 and sealingly engages against the valve seating end 32 by means of valve head 42. The tubular stem 36 further includes three stem orifices, of which two orifices 39, and 39a adjacent the valve head 42 are shown in FIGS. 3, and 5. The valve head 42 is of substantially larger diameter than the diameter of outer stem wall 41 of the tubular stem 36. The tubular stem 36 has an annular shoulder 44 which is in sealing engagement with the annular face 34 of the sleeve portion 26.

The closure member 16 of the present invention is generally of the type described in U.S. Pat. No. 3,132,774 to Soffer. The outer manipulative stem end 40 of the valve stem 36 of this invention is of length (less than about 1.25 cm) just sufficient to extend outwardly beyond the annular shoulder 44 and engage with actuating means 50 described below. This results in tubular valve stem 36 to be of shorter length than shown in U.S. Pat. No. 3,132,774, and commercially available from the Clayton Corporation. The short tubular valve stem 36 is necessary to minimize the post-dispensation bleeding of the composition through the central passage 38 of the valve stem 36.

The dispenser 10 as described hereinabove may be used for dispensing a proportioned amount of the composition by operation of the positive shut-off valve by tilting the manipulative stem end 40 of the stem 36 from its perpendicular position with a finger or a thumb (not shown). This manipulation of the stem 36 causes the valve to open as explained hereinbelow and allows for the dispensation of the liquid from the dispenser.

The dispenser 10 preferably comprises an actuating means 50 which is a generally L-shaped lever having an upright arm 46 and a horizontal arm 46. The horizontal arm 46 has preferably a central bore 48 which encircles and engages the outer manipulative end 40 of the valve stem 36. The actuating means 50 may assume any shape other than a generally L-shape so long as it is adapted to communicate with the outer manipulative end 40, be biased towards the deformable side walls 12, and actuate the closure member 16.

In the operation of the dispenser 10, as illustrated in FIGS. 4 and 5, the dispenser 10 containing the liquid composition 60 is held in an inverted position, i.e., the closure member adjacent the hand or the desired surface. A head space 62 contains the dual purpose pressure agent in the gaseous phase exhibiting the equilibrium vapor pressure of the composition. The upright arm 46 is depressed against the deformable side wall 12. This causes the horizontal arm 48 to pull the manipulative stem end 40 in a transverse direction, consequently causing the valve stem 36 to tilt (FIG. 5) from its perpendicular position (FIG. 4). The tilting of the stem 36 permits a gap to form between the counterbore 29 and the valve sealing face 32 in the region of the valve stem orifices 39 and 39a, allowing the contents to flow through the central passage 38 of the tubular valve stem 36. A proportioned amount, typically about 4–8 grams per second, of the post foaming liquid composition 60 contained in the dispenser 10 is, thereby, dispensed through a positive shut-off valve defined by operation of valve stem 36. The liquid is then spread with a single motion whereby the liquid develops into a foam (not shown) which turns into a rich lather on further rubbing. This method of use of the dispenser makes it possible to use only one hand to dispense the composition. During continued and prolonged use of the package of this invention, it may become necessary to shake the composition in the dispenser before dispensation.

The dispenser of the present invention is versatile in use in that it may further comprise mounting means (not shown) for mounting the dispenser on a wall of a shower stall, kitchen wall near a sink, or in the bathroom, or any other surface depending on the particular use to which the composition is being put. The mounting means may comprise a magnetic means, a Velcro™ means, and the like, or any conventional means which can be nailed or screwed onto the surface. The actuating means 50 as described hereinabove allows for one hand operation of the mounted dispenser, and contributes to the ease of its use and the convenience of the consumer.

While the invention has been illustrated and described as embodied in a dispenser for use with and without hand-operated lever mechanisms, it is not intended to be limited to the details shown, since various modifications and structural changes may be made without departing in any way from the spirit of the present invention.

What is claimed is:

1. A non-pressurized, non-compartmentalized dispenser of a deformable barrier material, the dispenser comprising a vessel formed with:

1) a deformable peripheral wall having an open neck;
   2) a positive shut off valve member comprising a tubular valve stem having a central dispensation passage for dispensing a liquid; and
   3) an actuating means which is biased towards the deformable barrier material of the dispenser;

and wherein said dispenser contains a composition comprising a stable, aqueous, self-foaming, self-leveling liquid consisting essentially of a mixture of:

(a) an effective amount of water to form a stable, aqueous, self-foaming, self-leveling liquid when mixed with components (b) and (c);
   (b) from about 0.1 to about 60 percent by weight of a surfactant wherein said surfactant is an anionic surfactant, a nonionic surfactant, an amphoteric surfactant, or a mixture of at least two of anionic, nonionic, amphoteric, and cationic surfactants, said surfactant selected to form a stable, self-foaming, self-leveling liquid when mixed with components (a) and (c); and
   (c) from about 1 to about 20 percent by weight of of a dual purpose pressure agent selected to form an integral part of the composition and selected to volatilize upon spreading the composition with a single motion, wherein said dual purpose pressure agent is
   (A) neopentane,
   (B) a mixture of at least one gaseous hydrocarbon having 4 carbon atoms and a nonvolatile silicone oil, or
   (C) a mixture of at least one gaseous hydrocarbon having 4 carbon atoms and at least one liquid hydrocarbon selected from iso-pentane, pentane, 2,3-dimethylbutane, hexane, iso-hexane, and mineral oil, said dual purpose pressure agent selected to form a stable, self-foaming, self-leveling liquid when mixed with components capable of providing said liquid composition with
      (i) a self-foaming property upon dispensation as a liquid from said container, and
      (ii) a vapor pressure of from about 0.1 psig to about 17 psig above atmospheric pressure at a temperature of about 22° C. in said container, said dual purpose pressure agent selected to form a stable, aqueous, self-foaming, self-leveling liquid when mixed with components (a) and (b);
   said resultant stable, aqueous, self-foaming, self-leveling liquid having a vapor pressure of from about 0.1 to about 17 psig in excess of atmospheric pressure at a temperature of 22° C. in said container, said resultant stable, aqueous, self-foaming, self-leveling liquid adapted to be dispensed in the form of a liquid from said container, whereby the liquid foams instantaneously on spreading.

2. The package of claim 1, wherein the actuating means comprises a lever which is generally L-shaped having an upright arm and a horizontal arm, the horizontal arm adapted to engage with the valve, and actuate the valve.

3. The dispenser of claim 1, wherein the dispenser dispenses from about 4 to about 8 grams per second of the liquid composition.

4. A method of use of the combination of claim 1, comprising: inverting the dispenser, operating the valve to dispense a proportioned amount of the composition, spreading and rubbing the composition whereby the composition develops into a lather in less than about one minute.

* * * * *